US009163035B2

United States Patent
Luo et al.

(10) Patent No.: US 9,163,035 B2
(45) Date of Patent: Oct. 20, 2015

(54) MELONINE BISINDOLE COMPOUNDS, PHARMACEUTICAL COMPOSITIONS, PREPARATION METHOD AND USE THEREOF

(75) Inventors: Xiaodong Luo, Kunming (CN); Tao Feng, Kunming (CN); Yan Li, Kunming (CN); Yuanyuan Wang, Kunming (CN); Xianghai Cai, Kunming (CN); Yaping Liu, Kunming (CN)

(73) Assignee: Kunming Institute of Botany, The Chinese Academy of Sciences, Kunming, Yunnan (CN)

( * ) Notice: Subject to any disclaimer, the term of this patent is extended or adjusted under 35 U.S.C. 154(b) by 651 days.

(21) Appl. No.: 13/508,277

(22) PCT Filed: Nov. 4, 2010

(86) PCT No.: PCT/CN2010/001775
§ 371 (c)(1),
(2), (4) Date: Jul. 16, 2012

(87) PCT Pub. No.: WO2011/054190
PCT Pub. Date: May 12, 2011

(65) Prior Publication Data
US 2012/0283284 A1    Nov. 8, 2012

(30) Foreign Application Priority Data

Nov. 4, 2009   (CN) .......................... 2009 1 0095137
May 11, 2010   (CN) .......................... 2010 1 0182905

(51) Int. Cl.
| | | |
|---|---|---|
| C07D 519/04 | (2006.01) | |
| A61K 31/4375 | (2006.01) | |
| A61K 31/475 | (2006.01) | |
| A61K 36/24 | (2006.01) | |
| C07D 519/00 | (2006.01) | |

(52) U.S. Cl.
CPC .......... *C07D 519/04* (2013.01); *A61K 31/4375* (2013.01); *A61K 31/475* (2013.01); *A61K 36/24* (2013.01); *C07D 519/00* (2013.01)

(58) Field of Classification Search
None
See application file for complete search history.

(56) References Cited

FOREIGN PATENT DOCUMENTS

CN    101704828 A    5/2010

OTHER PUBLICATIONS

Feng. Journal of Natural Products, 2010, 73, 22-26.*
Cancer prevention overview, http://www.cancer.gov/cancertopics/pdq/prevention/overview/patient, accessed Apr. 9, 2010.*
"Melodinus Henryi Craib", http://www.theplantlist.org/tpl/record/kew-124220, accessed Feb. 17, 2015.*
Hirasawa et al., "Bisleuconothine A, an eburnane-aspidosperma bisindole alkaloid from *Leuconotis griffithii*," *Bioorganic & Medicinal Chemistry Letters* 20(6): 2021-2024, Jan. 20, 2010.
Laguna et al., "Alkaloids from Roots of *Strempeliopsis strempelioides*—Structures of Strempeliopine and Strempeliopidine," *Planta Medica* 50(4): 285-288, 1984.
Li et al., "Indole Alkaloids of *Melodinus henryi* Craib," *Acta Botanica Sinica* 31(10): 792-797, 1989.

* cited by examiner

*Primary Examiner* — Noble Jarrell
(74) *Attorney, Agent, or Firm* — Seed IP Law Group PLLC

(57) ABSTRACT

The present invention relates to pharmaceutical technical field, to melonine bisindole compounds, pharmaceutical compositions thereof, and preparation methods thereof. Specifically, the present invention relates to melonine bisindole compounds of Formula I, pharmaceutically acceptable salts thereof, pharmaceutical compositions comprising the compounds or pharmaceutically acceptable salts thereof. The present invention further relates to method for preparing the melonine bisindole compounds of Formula I or pharmaceutically acceptable salts thereof, and the use of the melonine bisindole compounds of Formula I or pharmaceutically acceptable salts thereof in the manufacture of a medicament for the treatment or prophylaxis of cancers.

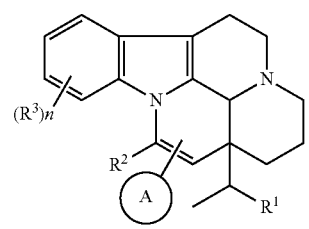

20 Claims, 3 Drawing Sheets

MELONINE BISINDOLE COMPOUNDS, PHARMACEUTICAL COMPOSITIONS, PREPARATION METHOD AND USE THEREOF

TECHNICAL FIELD

The present invention relates to pharmaceutical technical field, specifically, to melonine bisindole compounds of Formula I, pharmaceutically acceptable salts thereof, pharmaceutical compositions comprising the compounds or pharmaceutically acceptable salts thereof. The present invention further relates to a method for preparing the melonine bisindole compounds or pharmaceutically acceptable salts thereof, and uses of the melonine bisindole compounds or pharmaceutically acceptable salts thereof for the manufacture of medicaments for treatment or prophylaxis of cancers.

BACKGROUND ART

Cancers are the world's problem. In China, 1.6 millions cancer patients are newly increased per year, and 1.3 millions cancer patients died per year. At present, clinically used chemotherapeutics have certain therapeutical effects, but bring about tremendous physical pains and mental stress to patients due to their great toxicity, so that it is in urgent needs to develop novel antitumor drugs with definite therapeutical effects and less toxic and side effects.

CONTENTS OF THE INVENTION

With a plenty of experiments and unremitting efforts, the inventors of the present invention found new compounds, melonines A-D and derivatives thereof, and methods for preparing them. Thus, the following invention is provided.

One aspect of the present invention relates to a bisindole compound of Formula I or a pharmaceutically acceptable salt thereof, wherein,
ring A is a structure of the following Formula II, Formula III, or Formula IV:

each $R^1$ independently is hydrogen, hydroxyl, one or more halogen atoms, or oxo group; preferably, the oxo group is $C_{1-10}$ alkoxy, $C_{2-10}$ alkenoxy, or $C_{2-10}$ alkynoxy;

each $R^2$ independently is hydrogen, hydroxyl, $C_{1-10}$ alkyl, $C_{1-10}$ aldehyde group, $C_{1-10}$ alkylacyl, $C_{1-10}$ alkoxy, $C_{2-10}$ alkenoxy, $C_{2-10}$ alkynoxy, or one or more halogen atoms F, Cl, Br, or I; when the dash line to which the carbon atom linking $R^2$ of Formula I links is a single bond (in this case, the dash line together the below solid line represent a double bond, i.e., the carbon atom to which $R^2$ links is bonded by a double bond), the $R^2$ does not exist; when the dash line to which the nitrogen atom linking $R^2$ of Formula II links is a single bond (in this case, the dash line together the below solid line represent a double bond, i.e., the nitrogen atom to which $R^2$ links is bonded by a double bond), the $R^2$ does not exist;

each $R^3$ independently is hydrogen, hydroxyl, $C_{1-10}$ alkoxy, $C_{2-10}$ alkenoxy, $C_{2-10}$ alkynoxy or $C_{6-10}$ aryloxo;

each $R^4$ independently is hydrogen, hydroxyl, $C_{1-10}$ alkoxy, $C_{2-10}$ alkenoxy, $C_{2-10}$ alkynoxy or $C_{6-10}$ aryloxo;

each $R^5$ independently is hydrogen, hydroxyl, $C_{1-10}$ alkoxy, $C_{2-10}$ alkenoxy, $C_{1-10}$ acyloxo;

$R^6$, $R^7$, $R^8$ independently are hydrogen, hydroxyl, $C_{1-10}$ alkoxy, $C_{2-10}$ alkenoxy, $C_{2-10}$ alkynoxy or $C_{6-10}$ aryloxo; or $R^5$, $R^6$, $R^7$ and $R^8$ independently are oxo group; or a double bond is between the two carbon atoms to which $R^6$ and $R^7$ link, in this case, $R^6$ and $R^7$ do not exist;

n is 0, 1, 2, or 3.

In one embodiment of the present invention, $R^1$ is hydrogen.

In one embodiment of the present invention, n is 1.

In one embodiment of the present invention, $R^2$ is hydrogen or $C_{1-6}$ alkylacyl.

In one embodiment of the present invention, $R^3$ is hydroxyl or $C_{1-6}$ alkoxy.

The present invention preferably provides a bisindole compound of Formula I' or a pharmaceutically acceptable salt thereof:

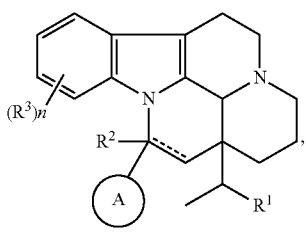

wherein $R^1$, $R^2$, $R^3$, n and ring A have the same meanings as in the above.

The present invention more preferably provides a bisindole compound of Formula V, Formula VI or Formula VII, or a pharmaceutically acceptable salt thereof:

V

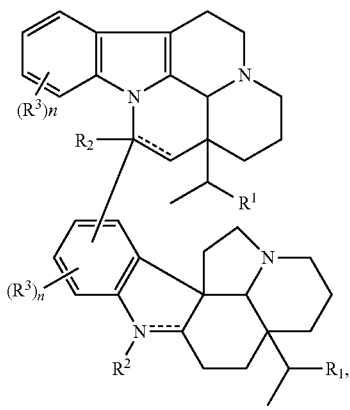

VI

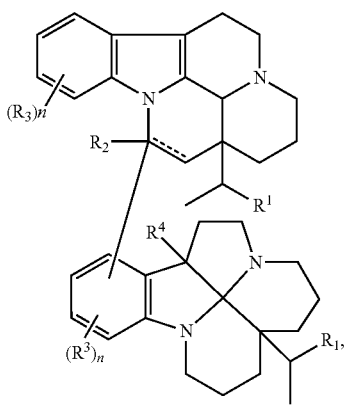

VII

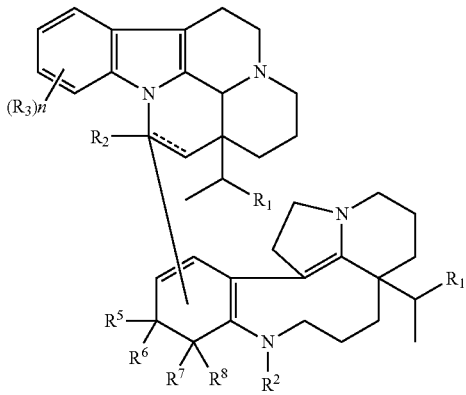

wherein $R^1$, $R^2$, $R^3$, $R^5$, $R^6$, $R^7$, $R^8$ and n have the same meanings as in the above.

The present invention further preferably provides a bisindole compound of Formula VIII, Formula IX or Formula X or a pharmaceutically acceptable salt thereof:

VIII

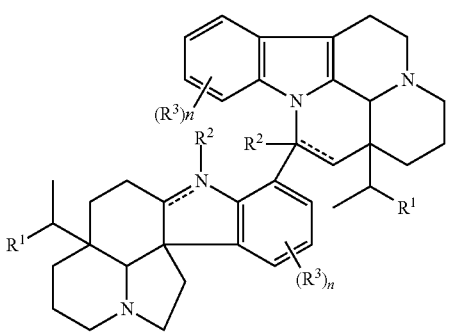

IX

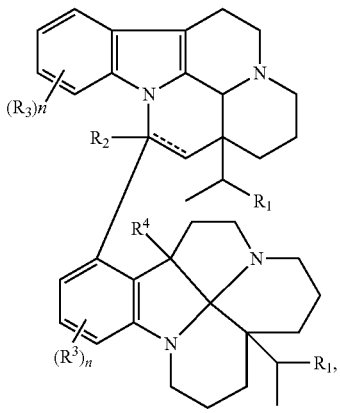

X

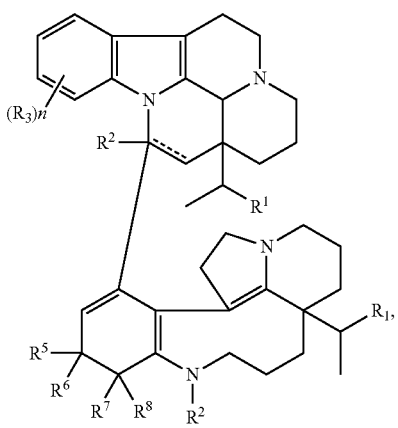

wherein $R^1$, $R^2$, $R^3$, $R^5$, $R^6$, $R^7$, $R^8$ and n have the same meanings as in the above.

The present invention most preferably provides melonine A, melonine B, melonine C or melonine D.

Another aspect of the present invention relates to a pharmaceutical composition, which comprises the bisindole compound of the present invention or a pharmaceutically acceptable salt thereof, and optionally comprises a pharmaceutically acceptable carrier or excipient.

Further another aspect of the present invention relates to a use of the bisindole compound of the present invention or a pharmaceutically acceptable salt thereof in the manufacture of a medicament for treatment or prophylaxis of a proliferative disease or disorder.

The proliferative disease or disorder is preferably a cancer, more preferably liver cancer, leukemia, pancreatic cancer, breast cancer or lung cancer.

In the present invention, the pharmaceutically acceptable salt is a salt formed with the compound and one or more organic acids or inorganic acids, wherein the organic acids include but are not limited to tartaric acid, citric acid, formic acid, acetic acid, oxalic acid, and the inorganic acids include but are not limited to hydrochloric acid, sulfuric acid, phosphoric acid, hydrobromide, nitrate.

In the description, the term "alkyl" refers to a straight or branched hydrocarbonyl, preferably having 1-10 carbon atoms, more preferably having 1-6 carbon atoms, more preferably having 1-4 carbon atoms. Representative examples include methyl, ethyl, propyl, isopropyl, n-butyl, isobutyl, tert-butyl, n-pentyl, and so on.

"Alkenyl" refers to a straight or branched aliphatic hydrocarbonyl with at least one double bond, preferably having 2-10 carbon atoms, more preferably having 2-6 carbon atoms, more preferably having 2-4 carbon atoms. Representative examples include ethenyl, propenyl, allyl, butenyl, pentadienyl, etc.

"Alkynyl" refers to a straight or branched aliphatic hydrocarbonyl with at least one triple bond, preferably having 2-10 carbon atoms, more preferably having 2-6 carbon atoms, more preferably having 2-4 carbon atoms. Representative examples include ethynyl, propynyl, butynyl, etc.

"Alkylacyl" refers to a group formed by removing hydroxyl from a straight or branched, cyclic or acyclic aliphatic carboxylic acid, preferably having 1-10 carbon atoms, more preferably having 1-6 carbon atoms, more preferably having 1-4 carbon atoms. Representative examples include formacyl, acetyl, propionyl, butyryl.

"Aryl" refers to a monocyclic or dicyclic aromatic group, which has 6-10 carbon atoms, may comprise 0-3 heteroatoms selected from O, S and N, and can fused with other rings. Representative examples include phenyl, naphtyl, furyl, quinolyl, etc.

"Oxo" or "oxo group" refers to an oxygen-containing substituent group, including but not being limited to: alkoxy, alkenoxy, alkynoxy, arylox, etc., wherein alkoxy is preferably $C_{1-10}$ alkoxy, alkenoxy is preferably $C_{2-10}$ alkenoxy, alkynoxy is preferably $C_{2-10}$ alkynoxy, aryloxo is preferably $C_{6-10}$ aryloxo.

A general method for preparing the bisindole compound of the present invention comprises: 1) deriving from plant and derivatization; and 2) chemical synthesis. The two methods are described in detail as follows.

1. Deriving from Plant and Derivatization

Melonines A, B, C and D can be prepared by the following steps:

They can be obtained by solvent extraction from a plant raw material of *Melodinus henryi Craib*, followed by separation and purification. If desired, they can form salts with a suitable acid, the suitable acid is selected from hydrochloric acid, hydrobromic acid, nitric acid, sulfuric acid, phosphoric acid, tartaric acid, citric acid, formic acid, acetic acid, oxalic acid or other suitable organic acids or inorganic acids.

The solvent extraction is preferably performed by reflux extraction or immersion extraction with an organic solvent, and the organic solvent is selected from $C_{1-6}$ alcohols, $C_{3-6}$ ketones, $C_{2-6}$ ethers, $C_{3-6}$ esters or $C_{1-6}$ halogenated hydrocarbons. Wherein, the $C_{1-6}$ alcohols include, for example, methanol, ethanol, n-propanol, isopropanol, n-butanol, isobutanol, tert-butanol, n-pentanol, isopentanol, cyclopentanol, n-hexanol, cyclohexanol, etc. The $C_{3-6}$ ketones include, for example, acetone, methyl ethyl ketone, methyl isobutyl ketone, etc. The $C_{2-6}$ ethers include, for example, methyl ether, ethyl ether, etc. The $C_{3-6}$ esters include, for example, ethyl formate, ethyl acetate, ethyl propionate, etc. The $C_{1-6}$ halogenated hydrocarbons include, for example, dichloromethane, chloroform, dichloroethane, etc.

If desired, the compound of Formula I can be further separated and purified, comprising acidifying the extract, allocating with an organic solvent, alkalifying the water layer, then extracting with an organic solvent again, and separating the organic solvent layer to obtain the compound.

If desired, a column chromatography can be used for further purification. The column chromatography can be a silica gel column chromatography, C18 column chromatography, ion exchange resin column chromatography, sephadex gel chromatography, etc. For example, a silica gel column chromatography can use a chloroform/methanol gradient elution, with chloroform/methanol in the ratios of 10:0, 20:1, 10:1, 8:1, 5:1, 3:1, 1:1

Specifically, whole plant of *Melodinus henryi Craib* is taken, dried, shredded, and is extracted with an alcohol for 1-4 times, 1-4 h per time, to obtain an alcohol extractum, then treated with acid/alkali to remove non-alkaloid substances, extracted with an organic solvent under alkaline condition, the organic extract layer is concentrated, the extractum is subjected to silica gel column chromatography, and chloroform/methanol is used as elution system to separate and obtain melonines A, B, C and D as four compounds of Formula I.

More specific method comprises: taking air-dried whole plant of *Melodinus henryi Craib*, heating with 70% ethanol at 70° C., extracting under refluxing for 3 times, recovering solvent, concentrating to reduce volume, adding 1% HCl to adjust pH to 2, extracting with ethyl acetate for 3 times, regulating the water layer with 10% aqueous ammonia to reach a pH of 9, then extracting with ethyl acetate for 3 times, concentrating the ethyl acetate layer, mixing the portion of ethyl acetate with silica gel, performing 700 g, 200-300 mesh silica gel column chromatography to produce 6 fractions: Frs 1-6, with chloroform/methanol gradient elution in the reatios of 10:0, 20:1, 10:1, 8:1, 5:1, 3:1, 1:1, separating Fr2 with petroleum ether/acetone=4/1 as eluent in silica gel 200 g column chromatography to obtain melonine A, separating Fr3 with chloroform/methanol=15:1 as eluant in silica gel 250 g column chromatography to obtain melonine D, separating Fr4 with chloroform/methanol=8:1 as eluant in silica gel 300 g column chromatography to obtain melonine C, eluting Fr6 firstly with chloroform/methanol=5:1 in silica gel 150 g column, then separating with methanol/water=2/8 in a reversed-phase silica gel RP-18, 100 g, column chromatography to obtain melonine B.

Optionally, the compounds of Formula I such as melonines A, B, C and D can be structurally modified and derivatized, for example, by introducing various substituent groups to indole rings, or by changing and modification at other substituents on the rings.

The substituents on the indole rings can be introduced by the method of Chinese Patent CN101108859A, wherein a compound of Formula V-1a such as melonine C is used as raw material, at a suitable temperature (−20° C. to 30° C.), reacted with a halogenating agent in a mixture solvent of anhydrous dichloroform and trifluoroacetic acid, to obtain halogenated compounds of Formulas V-1b, c, d, wherein V-1b and V-1d can be further converted into V-1c, then the reaction is carried out by heating to 40-150° C. under the catalysis of a transition metal to obtain the compound of Formula V (see: FIG. 1).

A fluorine can be introduced to the ethyl on the indole ring by a method, for example, disclosed by Jacquesy, J. C. (*J. Fluor. Chem.* 2006, 127, 1484-1487), wherein melonine C can be used as raw material, reacted with HF/SbF5 reagent at a suitable temperature in an organic solvent such as anhydrous dichloromethane or trichloromethane to obtain a fluorine-substituted general formula (see: FIG. 2).

Substituents on N of the indole ring can be introduced by a method, for example, disclosed by Kuboyama, et al. (*Proc. Nat. Acad. Sci. USA*, 2004, 101(33), 11966-11970), wherein melonine C, for example, is used as raw material, dissolved in acetic anhydride/formic acid (11:5), reacted under stirring for 1.5 h, then the reaction is terminated with aqueous ammonia, extraction is performed with dichloromethane, after the solvent is removed by evaporation, the crude product is purified to obtain a derivative in which H on N is acylated (see: FIG. 3).

2. Chemical Synthesis Method

The two indole monomers constituting the bisindole compound of Formula I to which substituents are introduced by the aforementioned methods to corresponding indole ring or other rings are modified if necessary, then coupled by acid catalysis in an alcohol (e.g., methanol, ethanol) at a sutiable temperature (e.g., room temperature to refluxing temperature, specifically, 20-80° C.), to obtain a compound of Formula I (see: FIG. 4).

The compounds of Formula I (melonines) or salts thereof can be administered via oral administration, and dosages thereof depend on different compounds. For an adult, 1-1000 mg per day is suitable.

When orally administered, the compound is firstly mixed with conventional pharmaceutically acceptable adjuvants, such as excipients, disintegrants, adhesives, lubricants, antioxidants, coating agents, coloring agents, flavoring agents, surfactants, etc., forming granules, capsules, tablets, etc. for administration; when non-orally administered, it can be administered in forms of injections, infusion solutions, or suppositories, etc. When preparing these dosage forms, conventional methods can be used.

SPECIFIC MODELS FOR CARRYING OUT THE INVENTION

Figure 1:
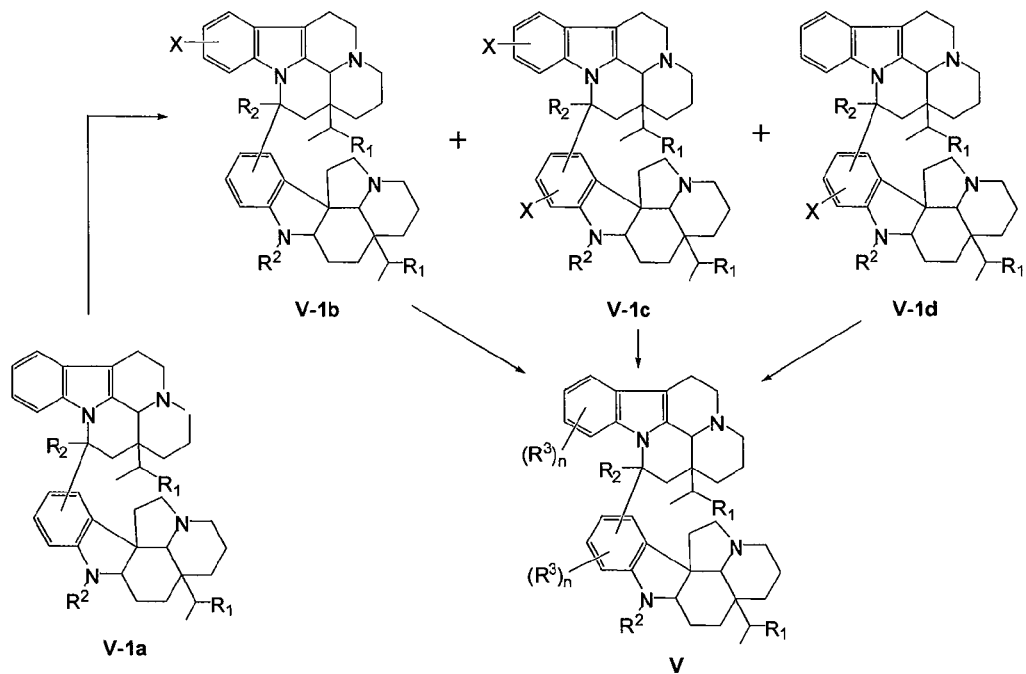
FIG. 1: an example of introducing a substituent to an indole ring of melonine compounds.

Some embodiments of the present invention are illustrated in detail in combination with the following examples. Those skilled in the art will understand that the following examples are merely used for illustrating the invention, instead of for limiting the scope of the invention. In the examples, if specific technologies or conditions are not given, technologies or conditions as described in documents in the art or in product specifications can be used. If reagents or instruments are not given their manufacturers, they are all conventional products commercially obtained in market.

Example 1

Preparation of Melonines A-D 12 kg of air-dried whole plant of *Melodinus henryi Craib* was extracted for 3 times with 70% ethanol by heating (70° C.) and refluxing, the solvent was recovered, the volume was reduced by concentration, 1% HCl was added to adjust pH to 2, ethyl acetate was used for extraction for 3 times, wherein the water layer was adjusted with 10% aqueous ammonia to reach a pH of 9, then was extracted with ethyl acetate for 3 times, the concentrated ethyl acetate layers were weighed as 77 g, the portion of ethyl acetate was mixed with an amount of silica gel, silica gel chromatography (700 g, 200-300 mesh, Qingdao Ocean Chemical Plant) was performed by dividing into 6 fractions (Frs 1-6), these fractions were gradiently eluted by chloroform/methanol (with chloroform/methanol in the ratios of 10:0, 20:1, 10:1, 8:1, 5:1, 3:1, 1:1). Fr2 (10 g) was separated with petroleum ether/acetone=4/1 as eluant by silica gel (200 g) column chromatography to obtain melonine A (10 mg), Fr3 (8 g) was separated with chloroform/methanol=15/1 as eluent by silica gel (250 g) column chromatography to obtain melonine D (23 mg), Fr4 (10 g) was separated with chloroform/methanol=8:1 as eluant by silica gel (300 g) column chromatography to obtain melonine C (2 g), Fr6 (4 g) was firstly eluted from silica gel (150 g) column with chloroform/methanol=5:1, then separated by reversed-phase silica gel (RP-18, 100 g) column chromatography (methanol/water=2/8), to obtain melonine B (18 mg).

The structures of melonines A-D are verified by the following Examples 2-5.

Example 2

Structure Verification of Melonine A

The chemical structure of melonine A is:

(II)

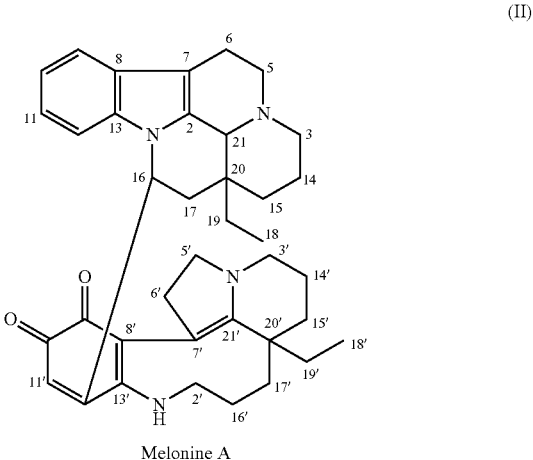 [SMILES: CCC12CCCNC3=C(C(=O)C(=O)C=C3C3CC4(CC)CCCN5CCc6c(n3c3ccccc63)C54)C3=C1N(CCC2)CC3]

Melonine A

Molecular weight 590, molecular formula $C_{38}H_{46}N_4O_2$. Optical rotation: $[\alpha]^{25.5}_D=+66°$. Red powder. Easily soluble in chloroform, acetone, methanol, slightly soluble in water.

The structure of melonine A was determined with its ultraviolet spectrum, infrared spectrum, mass spectrum and nuclear magnetic resonance spectrum, especially two-dimension nuclear magnetic resonance spectrum.

Ultraviolet spectrum data: UV λ(max) (MeOH): 500 (3.62), 354 (3.53), 270 (4.38), 240 (4.59).

Infrared spectrum: IR ν (max) (KBr): 3440, 2925, 1637, 1602, 1455.

Mass spectrum data: HR-ESI-MS (m/z): 591.3685 ([M+H]$^+$).

$^1$H NMR and $^{13}$C NMR data are shown in Table 1.

TABLE 1

| \$^1\$H NMR and $^{13}$C NMR data (CD$_3$OD) of melonine A | | |
|---|---|---|
| Atom No. | $\delta_H$ (in ppm, J in Hz) | $\delta_C$ (in ppm) |
| 2 | | 133.7 s |
| 3 | 2.28 (m); 2.52 (m) | 44.2 t |
| 5 | 3.31 (2H, m) | 50.6 t |
| 6 | 2.55 (m); 2.98 (m) | 17.0 t |
| 7 | | 105.5 s |
| 8 | | 128.6 s |
| 9 | 7.48 (d, 7.4) | 118.1 d |
| 10 | 7.10 (t, 7.4) | 119.5 d |
| 11 | 7.04 (t, 7.4) | 120.6 d |
| 12 | 7.00 (d, 7.4) | 111.5 d |
| 13 | | 135.0 s |
| 14 | 1.34 (m); 1.74 (m) | 20.5 t |
| 15 | 0.98 (ddd, 13.2, 4.0, 3.2); 1.38 (m) | 24.3 t |
| 16 | 5.35 (dd, 11.0, 4.6) | 48.6 d |
| 17 | 1.50 (m); 2.40 (m) | 42.0 t |
| 18 | 0.85 (t, 7.2) | 7.5 q |
| 19 | 1.47 (q, 7.2); 2.08 (q, 7.2) | 28.7 t |
| 20 | | 34.6 s |
| 21 | 3.91 (s) | 59.1 d |
| 2' | 2.25 (m); 2.62 (m) | 55.2 t |
| 3' | 2.43 (2H, m) | 53.7 t |
| 5' | 1.52 (m); 3.17 (d, 12.0) | 56.8 t |
| 6' | 2.75 (ddd, 13.6, 5.2, 4.0); 3.27 (m) | 22.5 t |
| 7' | | 122.6 s |
| 8' | | 128.2 s |
| 9' | 6.04 (s) | 131.7 d |
| 10' | | 149.1 s |
| 11' | | 176.0 s |
| 12' | | 184.0 s |
| 13' | | 143.6 s |
| 14' | 1.42 (m); 1.66 (m) | 22.5 t |
| 15' | 1.11 (m); 1.26 (m) | 34.3 t |
| 16' | 2.55 (2H, m) | 21.1 t |
| 17' | 1.57 (m); 1.80 (m) | 33.1 t |
| 18' | 0.79 (t, 7.4) | 7.7 q |
| 19' | 1.12 (2H, q, 7.4) | 31.8 t |
| 20' | | 37.2 s |
| 21' | | 123.1 s |

The above data in combination with 2D NMR analysis confirmed the chemical structure of melonine A is that shown in Formula II.

Example 3

Structure Verification of Melonine B

The chemical structure of melonine B is:

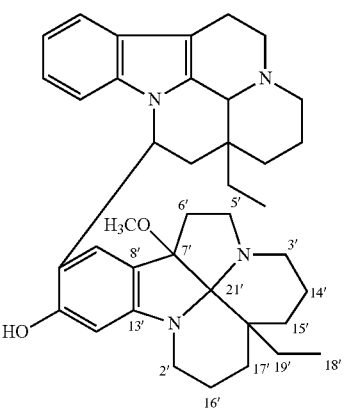

(III)

Melonine B

Molecular weight 606, molecular formula $C_{39}H_{50}N_4O_2$. Optical rotation: $[\alpha]^{25.5}_D=-237°$. Colorless oily product. Easily soluble in methanol, slightly soluble in water, acetone.

The structure of melonine B was determined with its ultraviolet spectrum, infrared spectrum, mass spectrum and nuclear magnetic resonance spectrum, especially two-dimension nuclear magnetic resonance spectrum.

Ultraviolet spectrum data: UV λ(max) (MeOH): 293 (3.60), 207 (4.49).

Infrared spectrum: IR ν (max) (KBr): 3418, 2926, 1624, 1456, 1384, 1319, 1180.

Mass spectrum data: HR-ESI-MS (m/z): 607.4013 ([M+H]$^+$).

$^1$H NMR and $^{13}$C NMR data are shown in Table 2.

TABLE 2

| \$^1\$H NMR and $^{13}$C NMR data (CD$_3$OD) of melonine B | | |
|---|---|---|
| Atom No. | $\delta_H$ (in ppm, J in Hz) | $\delta_C$ (in ppm) |
| 2 | | 131.8 s |
| 3 | 2.58 (t, 10.0); 2.80 (m) | 45.5 t |
| 5 | 3.46 (2H, m) | 52.0 t |
| 6 | 2.82 (m); 3.03 (m) | 17.6 t |
| 7 | | 105.2 s |
| 8 | | 129.2 s |
| 9 | 7.41 (d, 7.8) | 119.1 d |
| 10 | 6.94 (t, 7.8) | 120.6 d |
| 11 | 6.81 (t, 7.8) | 121.9 d |
| 12 | 6.63 (d, 7.8) | 113.0 d |
| 13 | | 137.6 s |
| 14 | 1.46 (m); 1.82 (overlap) | 20.6 t |
| 15 | 1.15 (m); 1.54 (overlap) | 24.3 t |
| 16 | 5.55 (dd, 11.0, 4.5) | 49.8 d |
| 17 | 1.67 (m); 2.37 (m) | 42.6 t |
| 18 | 0.93 (t, 7.2) | 7.6 q |
| 19 | 1.54 (overlap); 2.09 (m) | 29.2 t |
| 20 | | 36.3 s |
| 21 | 4.38 (s) | 61.1 d |
| 2' | 2.97 (m); 3.26 (m) | 58.1 t |
| 3' | 2.75 (m); 3.45 (m) | 63.6 t |
| 5' | 2.91 (m); 3.33 (m) | 64.4 t |
| 6' | 2.39 (m); 2.48 (dd, 13.5, 6.5) | 34.0 t |
| 7' | | 94.2 s |
| 8' | | 117.4 s |

TABLE 2-continued $^1$H NMR and $^{13}$C NMR data (CD$_3$OD) of melonine B

| Atom No. | $\delta_H$ (in ppm, J in Hz) | $\delta_C$ (in ppm) |
|---|---|---|
| 9' | 6.78 (s) | 124.9 d |
| 10' |  | 122.6 s |
| 11' |  | 158.5 s |
| 12' | 6.48 (s) | 98.3 d |
| 13' |  | 150.7 s |
| 14' | 1.70 (2H, m) | 26.3 t |
| 15' | 1.91 (m); 2.41 (m) | 26.8 t |
| 16' | 1.46 (m); 1.82 (overlap); | 19.9 t |
| 17' | 1.40 (m); 1.61 (m) | 33.2 t |
| 18' | 0.89 (3H, t, 7.4) | 7.1 q |
| 19' | 1.34 (2H, q, 7.4) | 34.4 t |
| 20' |  | 32.7 s |
| 21' |  | 103.6 s |
| OCH$_3$ | 2.68 (3H, s) | 52.9 q |

The above data in combination with 2D NMR analysis confirmed the chemical structure of melonine B is that shown in Formula III.

Example 4

Structure Verification of Melonine C

The chemical structure of melonine C is:

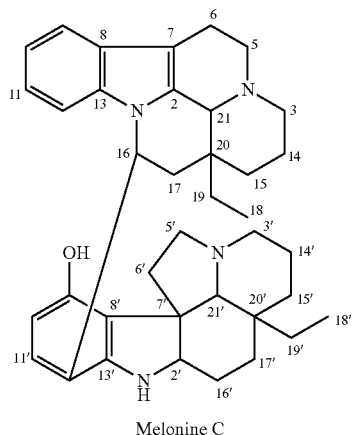

Melonine C (IV)

Molecular weight 576, molecular formula $C_{38}H_{48}N_4O$. Optical rotation: $[\alpha]^{25.5}_D = +19°$. Colorless powder, easily soluble in methanol, slightly soluble in water, acetone.

The structure of melonine C was determined with its ultraviolet spectrum, infrared spectrum, mass spectrum and nuclear magnetic resonance spectrum, especially two-dimension nuclear magnetic resonance spectrum.

Ultraviolet spectrum data: UV λ(max) (MeOH): 375 (2.88), 293 (3.75), 286 (3.74), 216 (4.56), 205 (4.58).

Infrared spectrum data: IR ν (max) (KBr): 3416, 3386, 2941, 1614, 1454, 1266.

Mass data: HR-EI-MS (m/z): 577.3898 ([M+H]$^+$).

$^1$H NMR and $^{13}$C NMR data are shown in Table 3.

TABLE 3

$^1$H NMR and $^{13}$C NMR data (CD$_3$OD) of melonine C

| Atom No. | $\delta_H$ (in ppm, J in Hz) | $\delta_C$ (in ppm) |
|---|---|---|
| 2 |  | 133.8 s |
| 3 | 2.50 (overlap); 2.61 (m) | 45.5 t |
| 5 | 3.33 (2H, m) | 52.0 t |
| 6 | 2.60 (m); 3.01 (m) | 17.8 t |
| 7 |  | 105.6 s |
| 8 |  | 129.7 s |
| 9 | 7.35 (d, 7.8) | 118.6 d |
| 10 | 6.89 (t, 7.8) | 120.1 d |
| 11 | 6.74 (t, 7.8) | 121.3 d |
| 12 | 6.59 (d, 7.8) | 112.9 d |
| 13 |  | 138.2 s |
| 14 | 1.42 (m); 1.79 (m) | 21.1 t |
| 15 | 1.22 (overlap); 1.44 (m) | 25.5 t |
| 16 | 5.09 (dd, 11.5, 4.6) | 52.0 d |
| 17 | 1.75 (m); 2.15 (m) | 43.2 t |
| 18 | 0.89 (3H, t, 8.0) | 7.6 q |
| 19 | 1.58 (q, 8.0); 2.09 (q, 8.0) | 29.7 t |
| 20 |  | 36.7 s |
| 21 | 4.09 (s) | 60.7 d |
| 2' | 3.45 (m) | 65.6 d |
| 3' | 2.50 (overlap); 3.17 (m) | 53.8 t |
| 5' | 2.23 (m); 3.13 (m) | 55.0 t |
| 6' | 1.79 (m); 2.19 (m) | 36.8 t |
| 7' |  | 54.4 s |
| 8' |  | 120.9 s |
| 9' | 6.63 (d, 8.0) | 127.9 d |
| 10' | 6.16 (d, 8.0) | 109.4 d |
| 11' |  | 149.6 s |
| 12' |  | 117.6 s |
| 13' |  | 154.7 s |
| 14' | 1.57 (m); 1.81 (m) | 22.3 t |
| 15' | 1.22 (over; ap); 1.70 (m) | 35.3 t |
| 16' | 1.85 (2H, m) | 29.3 t |
| 17' | 1.21 (m); 1.90 (m) | 23.5 t |
| 18' | 0.76 (t, 7.5) | 6.9 q |
| 19' | 1.24 (m); 1.62 (m) | 29.4 t |
| 20' |  | 36.3 s |
| 21' | 3.31 (s) | 70.9 d |

The above data in combination with 2D NMR analysis confirmed the chemical structure of melonine C is that shown in Formula IV.

Example 5

Structure Verification of Melonine D

The chemical structure of melonine D is:

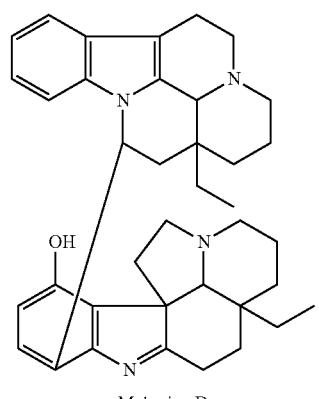

Melonine D (V)

Molecular weight 574, molecular formula $C_{38}H_{46}N_4O$. Optical rotation: $[\alpha]^{25.5}_D=+177°$. Colorless oily product. Easily soluble in methanol, slightly soluble in water, acetone.

The structure of melonine D was determined with its ultraviolet spectrum, infrared spectrum, mass spectrum and nuclear magnetic resonance spectrum, especially two-dimension nuclear magnetic resonance spectrum.

Ultraviolet spectrum data: UV λ(max) (MeOH): 375 (2.68), 292 (3.57), 284 (3.60), 204 (4.40).

Infrared spectrum data: IR ν (max) (KBr): 3421, 2927, 1585, 1454.

Mass spectrum data: HR-ESI-MS (m/z): 575.3734 ([M+H]$^+$).

$^1$H NMR and $^{13}$C NMR data are shown in Table 4.

TABLE 4

$^1$H NMR and $^{13}$C NMR data (CD$_3$OD) of melonine D

| Atom No. | δ$_H$ (in ppm, J in Hz) | δ$_C$ (in ppm) |
|---|---|---|
| 2 | | 134.8 s |
| 3 | 2.32 (m); 2.42 (m) | 44.6 t |
| 5 | 3.21 (2H, m) | 51.3 t |
| 6 | 2.53 (m); 2.98 (m) | 17.5 t |
| 7 | | 104.7 s |
| 8 | | 129.5 s |
| 9 | 7.67 (d, 8.0) | 118.3 d |
| 10 | 7.21 (t, 8.0) | 119.4 d |
| 11 | 7.10 (t, 8.0) | 120.5 d |
| 12 | 7.08 (d, 8.0) | 112.3 d |
| 13 | | 137.2 s |
| 14 | 1.14 (m); 1.62 (m) | 21.1 t |
| 15 | 0.99 (m); 1.24 (m) | 24.4 t |
| 16 | 6.38 (m) | 50.1 d |
| 17 | 1.94 (m); 2.33 (m) | 44.4 t |
| 18 | 0.67 (3H, t, 7.3) | 7.5 q |
| 19 | 1.36 (q, 7.3); 2.23 (overlap) | 29.1 t |
| 20 | | 35.2 s |
| 21 | 4.02 (s) | 59.8 d |
| 2' | | 193.0 s |
| 3' | 2.18 (m); 3.07 (m) | 52.3 t |
| 5' | 3.15 (2H, m) | 55.1 t |
| 6' | 2.19 (2H, m) | 32.4 t |
| 7' | | 62.7 s |
| 8' | | 131.2 s |
| 9' | | 153.5 s |
| 10' | 6.95 (d, 8.2) | 114.3 d |
| 11' | 7.14 (d, 8.2) | 127.2 d |
| 12' | | 126.2 s |
| 13' | | 154.5 s |
| 14' | 1.42 (m); 1.81 (m) | 22.2 t |
| 15' | 1.09 (m); 2.23 (overlap) | 33.3 t |
| 16' | 1.53 (m); 2.50 (m) | 29.6 t |
| 17' | 2.86 (m); 3.30 (m) | 24.1 t |
| 18' | 0.76 (t, 7.4) | 8.1 q |
| 19' | 1.19 (2H, m) | 30.8 t |
| 20' | | 36.6 s |
| 21' | 3.25 (s) | 75.2 d |

The above data in combination with 2D NMR analysis confirmed the chemical structure of melonine D is that shown in Formula V.

The preparation of pharmaceutically acceptable salts of the compounds of the present invention is illustrated in Examples 6-12.

Example 6

Preparation of Sulfates of Melonines A-D

Melonines A-D were prepared according to the method of Example 1, added with 4% sulfuric acid ethanol solution, pH=4, filtrated, dried, to prepare sulfates of melonines A-D.

Example 7

Preparation of Hydrochlorides of Melonines A-D

Melonines A-D were prepared according to the method of Example 1, added with 4% hydrochloric acid solution, pH=4, filtrated, dried, to prepare hydrochlorides of melonines A-D.

Example 8

Preparation of Phosphates of Melonines A-D

Melonines A-D were prepared according to the method of Example 1, added with 4% phosphoric acid solution, pH=4, filtrated, dried, to prepare phosphorates of melonines A-D.

Example 9

Preparation of Tartarates of Melonines A-D

Melonines A-D were prepared according to the method of Example 1, added with 4% tartaric acid solution, pH=4, filtrated, dried, to prepare tartarates of melonines A-D.

Example 10

Preparation of Citrates of Melonines A-D

Melonines A-D were prepared according to the method of Example 1, added with 4% citric acid solution, pH=4, filtrated, dried, to prepare citrates of melonines A-D.

Example 11

Preparation of Formates of Melonines A-D

Melonines A-D were prepared according to the method of Example 1, added with 4% formic acid acid solution, pH=4, filtrated, dried, to prepare formates of melonines A-D.

Example 12

Preparation of Oxalates of Melonines A-D

Melonines A-D were prepared according to the method of Example 1, added with 4% oxalic acid solution, pH=4, filtrated, dried, to prepare oxalates of melonines A-D.

Example 13

Preparation of 10-hydroxy-melonine C

Melonine C was dissolved in a mixture of anhydrous dichloromethane and trifluoroacetic acid at a suitable temperature (−20° C. to 30° C.), reacted with NBS to obtain 10-bromo-melonine C, then dissolved in water, reacted in the catalysis of transition metal by heating to 75° C. to obtain 10-hydroxy-melonine C.

Examples 14-19

Preparation of Other Melonine Derivatives

Figure 2:
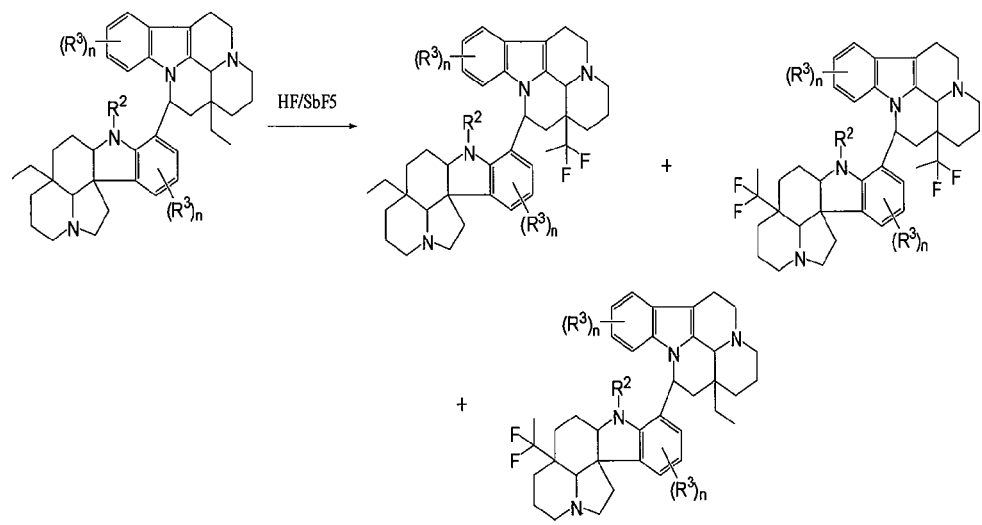
FIG. 2: an example of introducing fluorine to the ethyl of an indole ring of melonine compounds.
Figure 3:
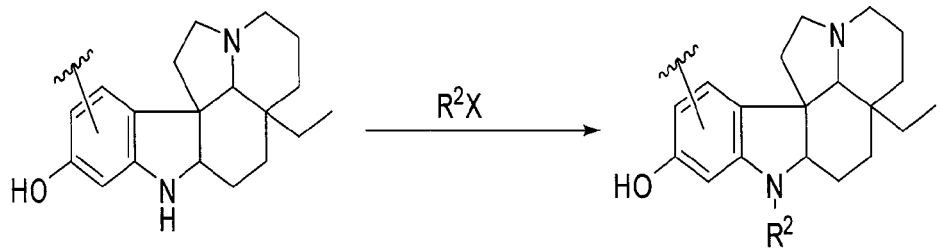
FIG. 3: an example of introducing a substituent to N of indole ring of melonine compounds.
Figure 4:
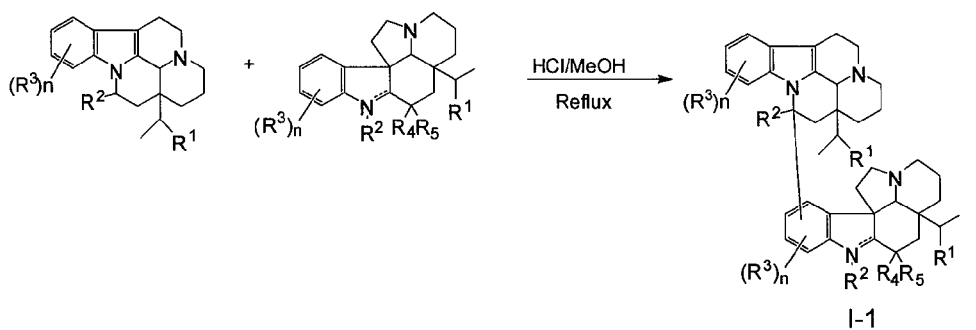
FIG. 4: final synthesis step of the compound of Formula I of the present invention.
Figure 4:
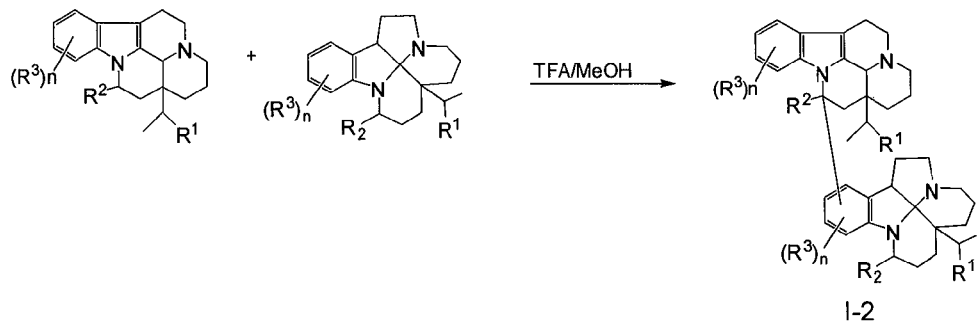
Figure 4:
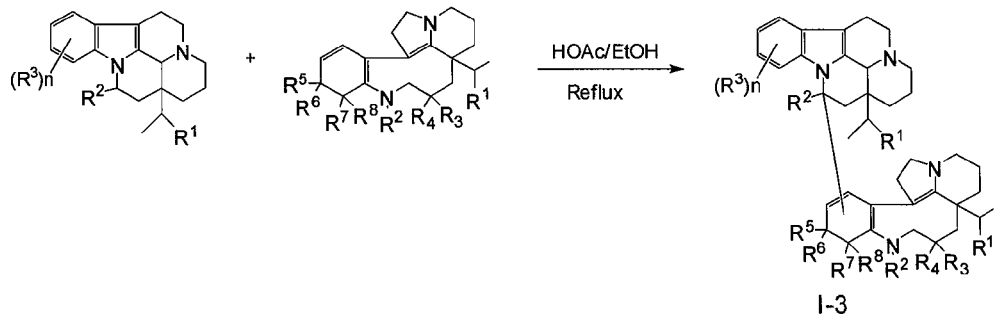

Similarly, the following compounds were prepared according to the methods of derivatization as shown in FIG. 1-3:

TABLE 5

Structure of the compound of Formula I

| Examples | Structural Formula | Name | MS(m/z) |
|---|---|---|---|
| 14 | | 10-methoxy-melonine A | 621 ([M + H]+) |
| 15 | | 10-acetyl-9',10'-dihydroxy-melonine A | 651 ([M + H]+) |
| 16 | | 1'-aldehydyl melonine C | 605 ([M + H]+) |

TABLE 5-continued

Structure of the compound of Formula I

| Examples | Structural Formula | Name | MS(m/z) |
|---|---|---|---|
| 17 | | 19-difluoro-melonine C | 613 ([M + H]+) |
| 18 | | 19-difloro-1'-aldehydyl melonine C | 641 ([M + H]+) |
| 19 | | 19-difluoro-melonine D | 611 ([M + H]+) |

The manufacture of preparations of the compounds or pharmaceutically acceptable salts is illustrated by the Examples 20-26.

Example 20

Manufacture of Injections

The melonines A, B, C and D were firstly prepared according to the method of Example 1, and the salts thereof were prepared by using organic acids (tartaric acid, citric acid, formic acid, oxalic acid, etc.) or inorganic acids (hydrochloric acid, sulfuric acid, phosphoric acid, etc.), then they were added with injection water, finely filtrated, packaged and sterilized to obtain injections.

Example 21

Manufacture of Powder Injections

The melonines A, B, C and D were firstly prepared according to the method of Example 1, and the salts thereof were prepared by using organic acids (tartaric acid, citric acid, formic acid, oxalic acid, etc.) or inorganic acids (hydrochloric acid, sulfuric acid, phosphoric acid, etc.), then they were dissolved in sterilized injection water, stirred to dissolve, filtered with sterile suction funnel, then finely filtered sterilely, subpackaged in two ampoules, freeze dried at low temperature, and sterilely sealed to obtain powder injections.

Example 22

Manufacture of Powders

The melonines A, B, C and D as obtained by separation and the salts prepared by using organic acids (tartaric acid, citric acid, formic acid, oxalic acid, etc.) or inorganic acids (hydrochloric acid, sulfuric acid, phosphoric acid, etc.) were added with excipients in a weight ratio of 9:1 to obtain powders.

Example 23

Manufacture of Tablets

The melonines A, B, C and D were firstly prepared according to the method of Example 1, and the salts thereof were prepared by using organic acids (tartaric acid, citric acid, formic acid, oxalic acid, etc.) or inorganic acids (hydrochloric acid, sulfuric acid, phosphoric acid, etc.), then they were added with excipients in a weight ratio of 1:5 to 1:10, tableted to obtain tablets.

Example 24

Manufacture of Oral Solutions

The melonines A, B, C and D were firstly prepared according to the method of Example 1, and the salts thereof were prepared by using organic acids (tartaric acid, citric acid, formic acid, oxalic acid, etc.) or inorganic acids (hydrochloric acid, sulfuric acid, phosphoric acid, etc.), then they were processed by conventional oral solution manufacture methods to form oral solutions.

Example 25

Manufacture of Capsules, Granules or Soluble Granules (1)

The melonines A, B, C and D were firstly prepared according to the method of Example 1, and the salts thereof were prepared by using organic acids (tartaric acid, citric acid, formic acid, oxalic acid, etc.) or inorganic acids (hydrochloric acid, sulfuric acid, phosphoric acid, etc.), then they were added with excipients in weight ratio of 5:1 to form capsules, granules or soluble granules.

Example 26

Manufacture of Capsules, Granules or Soluble Granules (2)

The melonines A, B, C and D were firstly prepared according to the method of Example 1, and the salts thereof were prepared by using organic acids (tartaric acid, citric acid, formic acid, oxalic acid, etc.) or inorganic acids (hydrochloric acid, sulfuric acid, phosphoric acid, etc.), then they were added with excipients in weight ratio of 3:1 to form capsules, granules or soluble granules.

Example 27

IC50 Test on Tumor Cells

I. Test Materials

1. Samples and Preparation Thereof:
The melonines A, B, C and D as prepared in Example 1 were separately dissolved with dimethyl sulfoxide (DMSO) to form 1 mg/ml storage solutions, stored away from light for standby use.
Cisplatin was used as positive control.
2. Cell Strains:
SK-BR-3, human breast cancer cell strain
SMMC7721, human liver cancer cell strain
HL-60, human leukemic cell strain
PANC-1, human pancreatic cancer cell strain
A549, human lung cancer cell strain II. Test Method (1) Inoculating cells: preparing cell suspension with culture medium comprising 10% fetal bovine serum (DMEM or RMPI1640), inoculating 96 wells plate with 10000-20000 cells per well (100 µl per well); if adherent cells are needed, inoculation and culture will be conducted 12 h in advance.

(2) adding a solution of compound to be tested (compound monomer of fixed concentration 40 µM for primary screening, crude extract of 100 µg/ml for primary screening, setting 5 concentrations for gradient repetitive screening for those compounds with a tumor cell growth inhibition rate of about 50% at the concentration for primary screening), final volume of 200 µl per well, and setting 3 repetitive wells for each treatment.

(3) Developing: culturing at 37° C. for 48 h, adding 20 µl of MTT solution to each well, continually incubating for 4 h, terminating cultivation, carefully discarding supernatant 100 µl to avoid cell lose, adding 20% SDS 100 µl to each well, incubating overnight (37° C.) to completely dissolve crystal.

(4) colorimetric analysis: selecting 595 nm wavelength, reading light absorption value of each well by enzyme-linked immunospot assay instrument (Bio-Rad 680), recording results, plotting cell growth curve using concentration as abscissa and cell survival rate as ordinate, and calculating IC50 value of compound using Reed and Muench method.

(5) Positive control: cisplatin.

III. Test Results

As shown in Table 6 as follows.

TABLE 6

Half Inhibitory concentrations (IC50, µM) of melonines A, B, C and D on human tumor cell strain growth

| Cell strain | Compound | | | | |
| --- | --- | --- | --- | --- | --- |
|  | Melonine A | Melonine B | Melonine C | Melonine D | Cisplatine |
| SK-BR-3 | 15.41 | 7.78 | 3.63 | 23.22 | 22.51 |
| SMMC7721 | 11.54 | 7.40 | 2.73 | 18.13 | 14.13 |
| HL-60 | 2.84 | 2.53 | 0.66 | 2.77 | 0.75 |

TABLE 6-continued

Half Inhibitory concentrations (IC50, µM) of melonines
A, B, C and D on human tumor cell strain growth

| Cell strain | Compound | | | | |
|---|---|---|---|---|---|
| | Melonine A | Melonine B | Melonine C | Melonine D | Cisplatine |
| PANC-1 | >40 | 14.45 | 3.77 | 23.41 | 19.47 |
| A549 | 22.07 | 14.70 | 3.01 | 11.07 | 26.54 |

IV. Conclusion

The results show that under the condition of the test, melonines A-D have IC50 values ranging from 0.66 to 23.41 µM for the growth of human breast cancer cell strain (SK-BR-3), human liver cancer cell strain (SMMC7721), human leukemic cell strain (HL-60), human pancreatic cancer cell strain (PANC-1), human lung cancer strain (A549). According to the proposed modified MTT method for evaluating antitumor active substance in Journal of Chinese Pharmaceutical Industry, 1993, 24: 455-457, ZHOU Jianjun, et al. the above data show that the compounds of the present invention have significant effects of inhibiting tumor cells/cancers.

Example 28

Test of Activity of Melonine C Against Nude Mouse-Transplanted Tumors

Test animals: female BALB/cA nude mice, 35-40 days, body weight 18-22 g, provided by Shanghai Slack, certificate no.: SCXK (Hu) 2007-0005. Divided into four groups:

Negative control group: 12 mice (intravenous injection with physiological saline, 3 times per week).

Administration group 1: 6 mice, intravenously administered with melonine C, in a dose of 20 mg/kg, 3 times per week.

Administration group 2: 6 mice, intravenously administered with melonine C, in a dose of 10 mg/kg, 3 times per week.

Administration group 3: 6 mice, intravenously administered with melonine C, in a dose of 2 mg/kg, 3 times per week.

The used melonine C was prepared in Example 1.

Transplanted tumors: human NCI-H460 nude mouse transplanted tumor, established by subcutaneously inoculating human NCI-H460 cell strain to female BALB/c nude mice (from Shanghai Slack Co., Ltd.). Inoculated cell number was $3 \times 10^6$, the formed transplanted tumor after inoculation was then passaged 3 times in body of nude mice before use. Specific method can be found in the following documents: Ripamonti M et al: In vivo anti-tumor activity of FCE 23762, a methoxymorpholinyl derivative of doxorubicin active on doxorubin-resistant tumor cells.; WANG Xingwang, XU Bin, New results of researches on models and methods for screening antitumore drugs, Edited by ZHENG Shu, Advances in Cancer Research in China (3): 110-113, Beijing: Military Medicine Press, 1998; and Waud W R, Corbett T, Plowman J, et al. In vivo methods. In: Teicher B A, eds. Anticancer drug development guide preclinical screening, clinical trials, and approval. Totowa: Humana Press, 1997: 59-213, and so on.

Test Methods:

The well-grown tumor tissues were cut into 1.5 mm³ pieces, inoculated into right-side armpit subcutaneously under sterile condition. The nude mouse transplanted tumore diameter was measured by vernier caliper, and the animals were grouped randomly when the tumore grew to 100-300 mm³. The antitumor effects of the compounds to be tested were observed by measuring tumor diameters. The number of measuring tumore diameters was 3 per week, and the mice were weighed simultaneously when each measurement was conducted. Melonine C was intravenously administered in doses of 20 mg/kg, 10 mg/kg, 2 mg/kg, separately, 3 times per week.

Detection indexes and calculation methods:

(1) tumor volume (TV), calculation formula is:

$$TV = 1/2 \times a \times b^2$$

wherein a, b represented length and width, respectively.

(2) relative tumor volume (RTV), calculation formula is:

$$RTV = TV_t/TV_0$$

wherein $TV_0$ was tumor volume when mice were grouped and administered (i.e., $d_0$), $TV_t$ was tumor volume when mice were measured each time.

(3) relative tumor proliferation rate, T/C (%), calculation formula is:

$$T/C\ (\%) = T_{RTV}/C_{RTV} \times 100\%$$

wherein, $T_{RTV}$ represents the RTV of administration group; $C_{RTV}$ represents the RTV of the negative control group.

In the test results, the relative tumore proliveration rate T/C (%) was used as evaluation index of antitumor activity.

Statistical Method:

The test data were presented in average values and standard derivations, and t-test was used as the statistical method.

Figure 5:
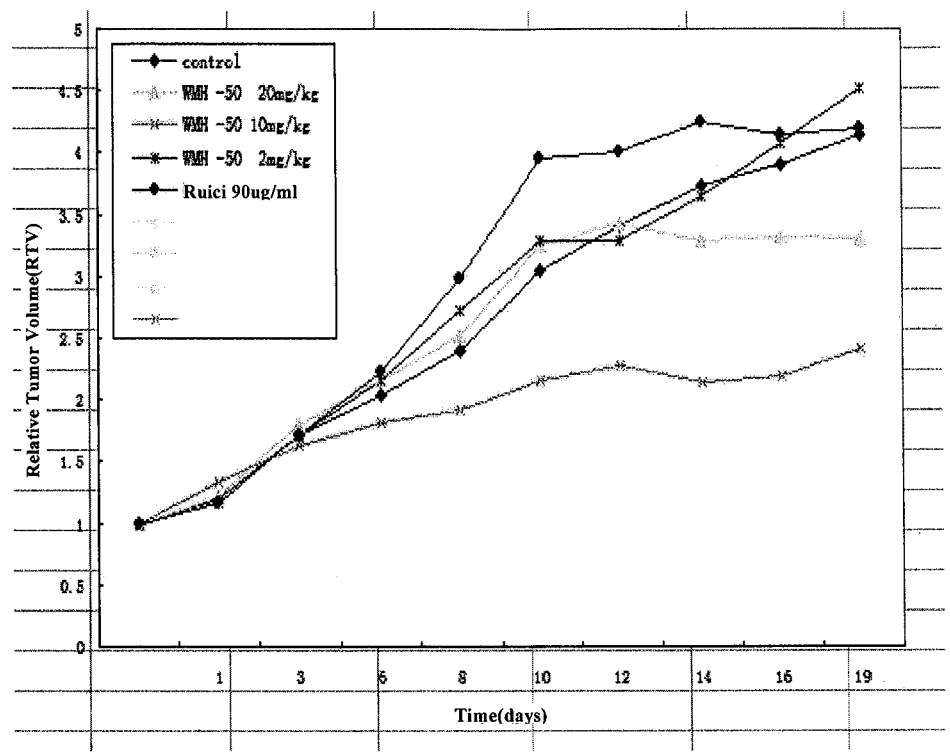
FIG. 5: a curve diagram of effects of melonine C on the growth of human cancer NCI-H460 nude mouse-transplanted tumor, wherein control represents negative control group, WXH-50 20 mg/kg represents administration group 1, WXH-50 10 mg/kg represents administration group 2, WXH-50 2 mg/kg represents administration group 3; Ruici is another administration sample, irrelevant to the present invention.
Figure 6:
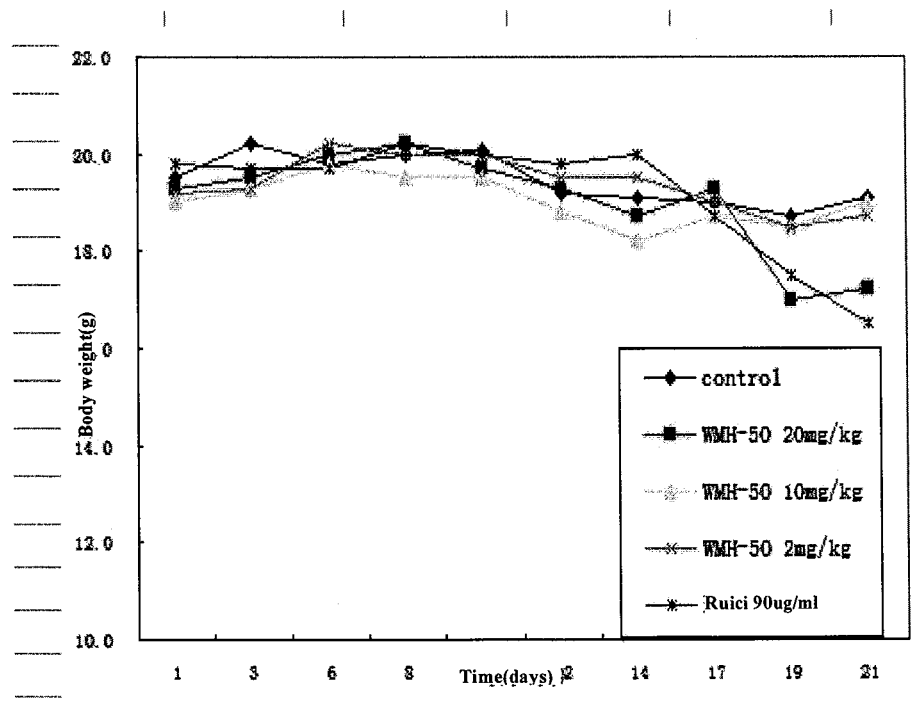
FIG. 6: a curve diagram of effects of melonine C on the weight of human cancer NCI-H460 nude mouse, wherein control represents negative control group, WXH-50 20 mg/kg represents administration group 1, WXH-50 10 mg/kg represents administration group 2, WXH-50 2 mg/kg represents administration group 3; Ruici is another administration sample, irrelevant to the present invention.

Results:

The intravenous administration of 10 mg/kg melonine C had inhibition effects on the growth of human NCI-H460 nude mouse transplanted tumor, and T/C (%) was 56.41 (the results are shown in FIG. 5); the 3 doses of melonine C had no significant effect on the body weight of human NCI-H460 nude mice (results are shown in FIG. 6).

Example 29

Acute Toxicity Test of Melonine C

Animal lines: healthy mice, rats. Age was 7-9 weeks. In the same batch of tests, the initial body weight of mice or rats should not be greater or less than the average body weight by 20%. The animals were observed at least for one week befor test, and the behavior, diet, body weight and spirit conditions were recorded.

The used melonine C was prepared in Example 1.

Administration route: tail vein injection for both rats and mice.

Measurement of median lethal dose (LD50):

Maximum tolerated dose (MTD) test method: MTD refers to a dose that causes significant toxic reaction without death in animals.

Test observation: the observation was performed for one week after administered with the drug to be tested, the time of appearance and disappearance of various toxic reactions was carefully observed and recorded for each animal. The observation and recording were performed twice on the day of administering the drug to be tested, then once per day in the following days. The contents to be observed and recorded include skin, mucous membrane, coat color, eyes, respiration, circulation, behaviors of autonomic and central nervous systems, etc. Before the drug to be tested was administered, one week after the drug to be tested was administered, when the animal died, and when the test was ended, the animals were weighed to get their body weights. All animals, including dead or executed animals, were subjected to autopsy, and histopathologic examination was performed for organs with abnormal autopsy results.

Results:

Melonine C: LD50: 32 mg/kg (mice), MTD: 22 mg/kg.

Melonine C: LD50: 20 mg/kg (rats).

The toxic animal immediately behaved accelerated breathing, ataxia, convulsions, or even died, the toxic reaction was alleviated with the decrease of dose, and the survival animals returned to normal after 5 min, did not die within one week, the survival animals were dissected after 7 days, and all main organs were normal without pathological changes.

Although the specific models for carrying out the invention have been described in detail, those skilled in the art will understand these details can be modified and changed according to all teachings in the art, and these changes are within the protection scope of the present invention. The whole scope of the present invention is given by the attached claims and any equivalents thereof.

What is claimed is:

1. A bisindole compound of Formula I or a pharmaceutically acceptable salt thereof,

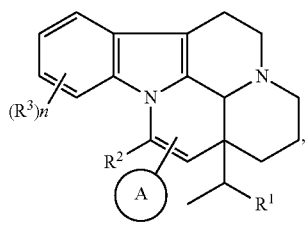

wherein, ring A has a structure of Formula III:

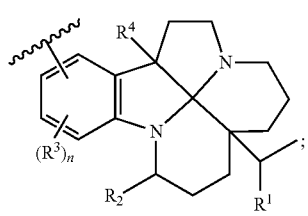

each $R^1$ independently is hydrogen, hydroxyl, one or more halogen atoms, or oxo group;
each $R^2$ independently is hydrogen, hydroxyl, $C_{1-10}$ alkyl, $C_{1-10}$ aldehyde group, $C_{1-10}$ alkylacyl, $C_{1-10}$ alkoxy, $C_{2-10}$ alkenoxy, $C_{2-10}$ alkynoxy, or one or more halogen atoms F, Cl, Br, or I; or when the dash line to which the carbon atom linking $R^2$ in Formula I links is a single bond, the $R^2$ does not exist;
each $R^3$ independently is hydrogen, hydroxyl, $C_{1-10}$ alkoxy, $C_{2-10}$ alkenoxy, $C_{2-10}$ alkynoxy or $C_{6-10}$ aryloxo;
each $R^4$ independently is hydrogen, hydroxyl, $C_{1-10}$ alkoxy, $C_{2-10}$ alkenoxy, $C_{2-10}$ alkynoxy or $C_{6-10}$ aryloxo;
each n is independently 0, 1, 2, or 3,
wherein the bisindole compound of Formula I is not melonine B having the structure:

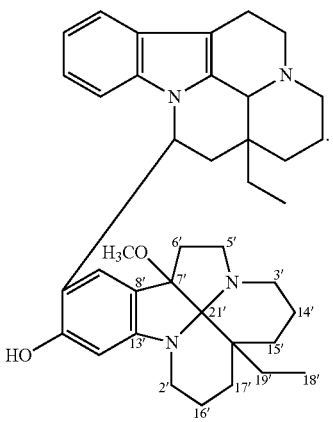 [SMILES: CCC12CCCN3CCc4c(n(c5ccccc45)C(c4cc5c(cc4O)N4CCCC6(CC)CCCN7CCC5(OC)C746)C1)C32]

2. The bisindole compound or a pharmaceutically acceptable salt thereof according to claim 1, wherein each $R^1$ is hydrogen.

3. The bisindole compound or a pharmaceutically acceptable salt thereof according to claim 1, wherein each n is 1.

4. The bisindole compound or a pharmaceutically acceptable salt thereof according to claim 1, wherein each $R^2$ is independently hydrogen or $C_{1-6}$ alkylacyl.

5. The bisindole compound or a pharmaceutically acceptable salt thereof according to claim 1, wherein each $R^3$ is independently hydroxy or $C_{1-6}$ alkoxy.

6. The bisindole compound or a pharmaceutically acceptable salt thereof according to claim 1, which has a structure of Formula I':

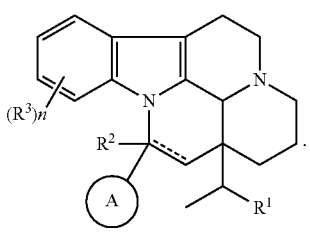

7. The bisindole compound or a pharmaceutically acceptable salt thereof according to claim 6, wherein the bisindole compound has a structure of Formula VI:

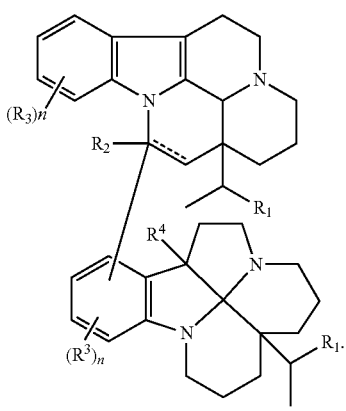

8. The bisindole compound or a pharmaceutically acceptable salt thereof according to claim 7, which has a structure of Formula IX:

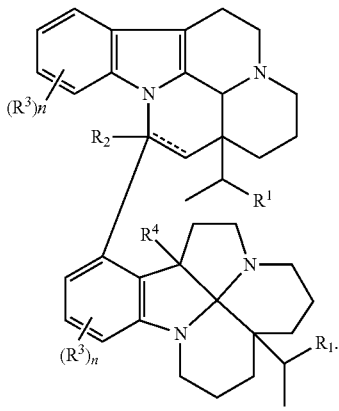

IX

9. The bisindole compound or a pharmaceutically acceptable salt thereof according to claim 1, wherein the pharmaceutically acceptable salt is one or more selected from hydrochlorides, hydrobromides, nitrates, sulfates, phosphates, tartarates, citrates, formats, acetates, and oxalates.

10. A method for preparing the bisindole compound or a pharmaceutically acceptable salt thereof according to claim 1, wherein the method comprising: using plant of *Melodinus henryi Craib* as raw material; and optionally, forming the bisindole compound in a salt form with one or more suitable acid, wherein, the suitable acid is hydrochloric acid, hydrobromic acid, nitric acid, sulfuric acid, phosphoric acid, tartaric acid, citric acid, formic acid, acetic acid, or oxalic acid.

11. The method according to claim 10, comprising the following steps:
combining whole plant of *Melodinus henryi Craib* with 40-95% ethanol;
heating and refluxing the combined whole plant and 40-95% ethanol at 40-80° C. to provide an extract;
concentrating the extract while adding acid to adjust pH value to 1.0-5.0,
extracting with an organic solvent,
alkalifying the water layer to adjust pH value to 8.0-11.0,
extracting with an organic solvent again,
concentrating the organic solvent layer,
conducting a silica gel column chromatography,
eluting with chloroform/methanol gradiently, with chloroform/methanol in the ratios of 10:0, 20:1, 10:1, 8:1, 5:1, 3:1, or 1:1.

12. A pharmaceutical composition, comprising the bisindole compound or a pharmaceutically acceptable salt thereof according to claim 1; optionally, further comprising a pharmaceutically acceptable adjuvant.

13. A method for treating a proliferative disease or disorder in a human or animal, comprising administering an effective amount of the bisindole compound or a pharmaceutically acceptable salt thereof according to claim 1, wherein the proliferative disease or disorder is a cancer, wherein the cancer is breast cancer, hepatocellular carcinoma, myeloid leukemia, pancreatic cancer, or lung cancer.

14. The bisindole compound or a pharmaceutically acceptable salt thereof according to claim 1, wherein the oxo group is C1-10 alkoxy, C2-10 alkenoxy, or C2-10 alkynoxy.

15. A pharmaceutically acceptable salt of melonine B, wherein melonine B is:

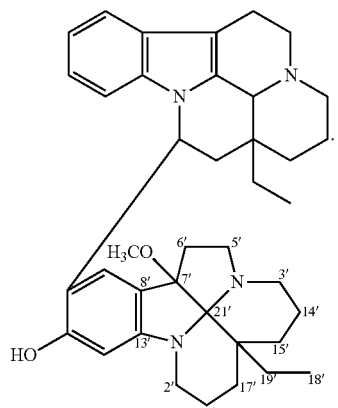

16. The pharmaceutically acceptable salt of melonine B according to claim 15, wherein the pharmaceutically acceptable salt is one or more selected from hydrochlorides, hydrobromides, nitrates, sulfates, phosphates, tartarates, citrates, formats, acetates, and oxalates.

17. A pharmaceutical composition, comprising the pharmaceutically acceptable salt of melonine B according to claim 15; optionally, further comprising a pharmaceutically acceptable adjuvant.

18. The pharmaceutical composition according to claim 17, wherein the pharmaceutically acceptable salt of melonine B is one or more selected from hydrochlorides, hydrobromides, nitrates, sulfates, phosphates, tartarates, citrates, formats, acetates, and oxalates.

19. A method for treating breast cancer, hepatocellular carcinoma, myeloid leukemia, pancreatic cancer, or lung cancer in a human or animal, comprising administering an effective amount of the pharmaceutically acceptable salt of melonine B according to claim 15 or melonine B, wherein melonine B has the structure of:

20. The method according to claim 19, wherein the pharmaceutically acceptable salt of melonine B is one or more selected from hydrochlorides, hydrobromides, nitrates, sulfates, phosphates, tartarates, citrates, formats, acetates, and oxalates.

* * * * *